(12) United States Patent
Bean et al.

(10) Patent No.: US 12,403,031 B2
(45) Date of Patent: Sep. 2, 2025

(54) EXTERNAL ANKLE BRACE

(71) Applicant: TayCo Brace, Inc., South Bend, IN (US)

(72) Inventors: Michael W. Bean, South Bend, IN (US); Frederick John Ferlic, South Bend, IN (US)

(73) Assignee: TayCo Brace, Inc., South Bend, IN (US)

( * ) Notice: Subject to any disclaimer, the term of this patent is extended or adjusted under 35 U.S.C. 154(b) by 0 days.

(21) Appl. No.: 17/888,428

(22) Filed: Aug. 15, 2022

(65) Prior Publication Data
US 2022/0395389 A1 Dec. 15, 2022

Related U.S. Application Data

(63) Continuation of application No. 15/642,430, filed on Jul. 6, 2017, now Pat. No. 11,413,180, which is a
(Continued)

(51) Int. Cl.
*A61F 5/01* (2006.01)
*A43B 7/20* (2006.01)

(52) U.S. Cl.
CPC .............. *A61F 5/0127* (2013.01); *A43B 7/20* (2013.01); *A61F 5/0195* (2013.01)

(58) Field of Classification Search
CPC .... A43B 7/20; A43B 7/18; A43B 3/16; A43B 3/163; A43B 3/18; A43B 3/20;
(Continued)

(56) References Cited

U.S. PATENT DOCUMENTS 1,692,896 A 11/1928 Hilgert
4,320,748 A * 3/1982 Racette ................. A61F 5/0585
602/23
(Continued)

OTHER PUBLICATIONS

Martin Alfuth et al., "Biomechanical Comparison of 3 Ankle Braces With and Without Free Rotation in the Sagittal Plane," Journal of Athletic Training, Oct. 2014, pp. 608-616, vol. 49, No. 5.
(Continued)

*Primary Examiner* — Keri J Nelson
(74) *Attorney, Agent, or Firm* — Piloff Passino & Cosenza LP; Martin J. Cosenza

(57) ABSTRACT

An external ankle brace for restricting movement of an ankle in a first direction and permitting movement of the ankle in a second direction includes a rigid heel enclosure having a rear portion and a forward portion. A lateral upright extension is perpendicular to the rigid heel enclosure and is attached to the lateral sidewall. A medial upright extension is perpendicular to the rigid heel enclosure and is attached to the medial sidewall. At least a chosen one of the lateral and medial upright extensions is selectively pivotally attached to a corresponding lateral or medial sidewall and includes a pivot prevention feature configured to selectively prevent pivoting of the chosen one of the lateral and medial upright extensions with respect to the corresponding lateral or medial sidewall.

56 Claims, 9 Drawing Sheets

Related U.S. Application Data continuation-in-part of application No. 15/074,339, filed on Mar. 18, 2016, now abandoned.

(60) Provisional application No. 62/135,823, filed on Mar. 20, 2015.

(58) Field of Classification Search
CPC ........ A61F 5/00; A61F 5/0127; A61F 5/0195; A61F 5/0111; A41D 17/00; A41D 17/005
USPC .......................................................... 602/5
See application file for complete search history.

(56) References Cited

U.S. PATENT DOCUMENTS

| | | | |
|---|---|---|---|
| 4,510,927 A | 4/1985 | Peters | |
| 4,517,968 A | 5/1985 | Greene et al. | |
| 4,611,414 A | 9/1986 | Vogel | |
| 4,771,768 A | 9/1988 | Crispin | |
| 4,834,078 A | 5/1989 | Biedermann | |
| 5,031,607 A | 7/1991 | Peters | |
| 5,069,202 A * | 12/1991 | Prock | A61F 5/0127 602/27 |
| 5,094,232 A | 3/1992 | Harris et al. | |
| 5,429,588 A | 7/1995 | Young et al. | |
| 5,454,173 A * | 10/1995 | Falguere | A43B 5/0411 36/117.2 |
| 5,571,078 A | 11/1996 | Malewicz | |
| 5,676,642 A | 10/1997 | Peters | |
| 5,792,087 A | 8/1998 | Pringle | |
| 5,921,945 A | 7/1999 | Gray | |
| 5,992,057 A | 11/1999 | Monti | |
| 6,053,884 A | 4/2000 | Peters | |
| 6,267,742 B1 | 7/2001 | Krivosha et al. | |
| 6,299,587 B1 * | 10/2001 | Birmingham | A61F 5/0127 602/5 |
| 6,409,695 B1 | 6/2002 | Connelly | |
| 6,602,215 B1 | 8/2003 | Richie, Jr. | |
| 6,669,659 B2 * | 12/2003 | Dittmer | A61F 5/05841 602/5 |
| 6,689,081 B2 | 2/2004 | Bowman | |
| 7,127,836 B1 | 10/2006 | Jamison | |
| 7,624,519 B1 | 12/2009 | Thorne | |
| 7,785,283 B1 | 8/2010 | Bledsoe | |
| 9,259,343 B2 | 2/2016 | Newman | |
| 9,622,898 B1 * | 4/2017 | Weber | A61F 5/0104 |
| 9,844,455 B2 | 12/2017 | Bradshaw | |
| 11,413,180 B2 * | 8/2022 | Bean | A61F 5/0127 |
| 2001/0051780 A1 | 12/2001 | Birmingham | |
| 2004/0015112 A1 * | 1/2004 | Salutterback | A61F 5/0127 602/22 |
| 2004/0034316 A1 | 2/2004 | Castro | |
| 2004/0225241 A1 | 11/2004 | Scheinberg et al. | |
| 2009/0287127 A1 | 11/2009 | Hu et al. | |
| 2010/0137770 A1 | 6/2010 | Ingmundarson et al. | |
| 2011/0173841 A1 | 7/2011 | McDuff | |
| 2012/0145167 A1 | 6/2012 | Davis | |
| 2013/0226059 A1 | 8/2013 | Morris | |
| 2014/0066829 A1 | 3/2014 | Drillio | |
| 2015/0088044 A1 | 3/2015 | Walborn et al. | |
| 2015/0216703 A1 * | 8/2015 | Madden | A61F 5/0127 602/7 |
| 2015/0313743 A1 * | 11/2015 | Ostergard | A43C 1/00 602/27 |
| 2016/0029743 A1 | 2/2016 | Cavaliere et al. | |
| 2016/0235578 A1 * | 8/2016 | Romo | A61F 5/0127 |
| 2016/0270944 A1 | 9/2016 | Bean | |
| 2021/0298939 A1 | 9/2021 | Bean et al. | |

OTHER PUBLICATIONS

Patria A. Hume et al., "Effectiveness of External Ankle Support, Bracing and Taping in Rugby Union," Sports Medicine, May 1998, pp. 285-312, vol. 25, No. 5.

The Free Dictionary by Farlex, "plastically," https://www.thefreedictionary.com/plastically.

International Search Report and Written Opinion for PCT/US22/22018, mailed Jul. 25, 2022.

* cited by examiner

EXTERNAL ANKLE BRACE

CROSS-REFERENCE TO RELATED APPLICATIONS

This application is a continuation of U.S. patent application Ser. No. 15/642,430, filed Jul. 6, 2017, which is a continuation-in-part of U.S. patent application Ser. No. 15/074,339, filed 18 Mar. 2016, which claims the benefit of U.S. Provisional Patent Application Ser. No. 62/135,823, which was filed on 20 Mar. 2015. Each of these applications is incorporated herein by reference, in its entirety, for all purposes.

TECHNICAL FIELD

The disclosure pertains generally to preventative and rehabilitative equipment, and more particularly to an ankle brace.

BACKGROUND

In the world of sports, ankle injuries are among the most common cause of lost playing time in a sporting career, with a typical ankle injury leaving the athlete out of competition for up to a month. Ankle sprains occur when there is a rapid shifting of weight from one direction to another. The force generated from the movement causes the foot to roll either inwards, which is known as inversion rotation; or outwards, which is known as eversion rotation. Both the inversion and eversion motion of the ankle cause the ligaments on the outside of the ankle to stretch or tear depending on the force that was generated during the movement.

Current braces vary from woven fabric that acts as a glove and wraps around the ankle, to rigid plastic uprights that are strapped around the ankle. The woven fabric braces typically are made of a thin fabric that envelope the ankle and are laced together to support the ankle from both inversion and eversion rotation. The main drawback with these types of braces is that the material lacks the resistance to prevent the ankle from rolling under intense forces. Further, fabric braces also have to be worn within the shoe, which causes the shoe to fit tighter or, in some cases, forces the user to move up a shoe size in order to wear the brace. In terms of the rigid uprights braces, these braces are typically much heavier than the fabric braces and also much larger. Fitting a rigid brace into a tight shoe almost never works, which forces the user to move up to the next shoe size to accommodate for the bulkiness of the brace. When the user moves up a shoe size, the shoe is no longer sized correctly for the foot and thus loses a portion of its intended use and purpose. These braces leave the user at risk for further injury because either the brace isn't strong enough to support the ankle or the shoe isn't fitted properly to the foot.

SUMMARY

In an embodiment, an external ankle brace for restricting movement of an ankle in a first direction and permitting movement of the ankle in a second direction is provided. The external ankle brace is disposed on the exterior of a shoe and the shoe has a heel portion, a sole, and oppositely disposed sides. A rigid heel enclosure has a rear portion and a forward portion. The rear portion is for receiving the heel of the shoe. The forward portion has a medial sidewall and a lateral sidewall for surrounding the sides of the shoe. A lateral upright extension is perpendicular to the rigid heel enclosure and is attached to the lateral sidewall. A medial upright extension is perpendicular to the rigid heel enclosure and is attached to the medial sidewall. A lower fastening system comprises at least one connecting strap for connecting the lateral sidewall to the medial sidewall underneath the sole of the shoe. An upper fastening system comprises at least one connecting strap for removably connecting the lateral sidewall to the medial sidewall across the top of the shoe. At least a chosen one of the lateral and medial upright extensions is selectively pivotally attached to a corresponding lateral or medial sidewall. The chosen one of the lateral and medial upright extensions includes a pivot prevention feature configured to selectively prevent pivoting of the chosen one of the lateral and medial upright extensions with respect to the corresponding lateral or medial sidewall.

BRIEF DESCRIPTION OF THE DRAWINGS

These and other features, aspects, and advantages of the present disclosure will become better understood when the following detailed description is read with reference to the accompanying drawings in which like numerals are used to indicate like structure throughout the various figures.

DETAILED DESCRIPTION

Figure 1:
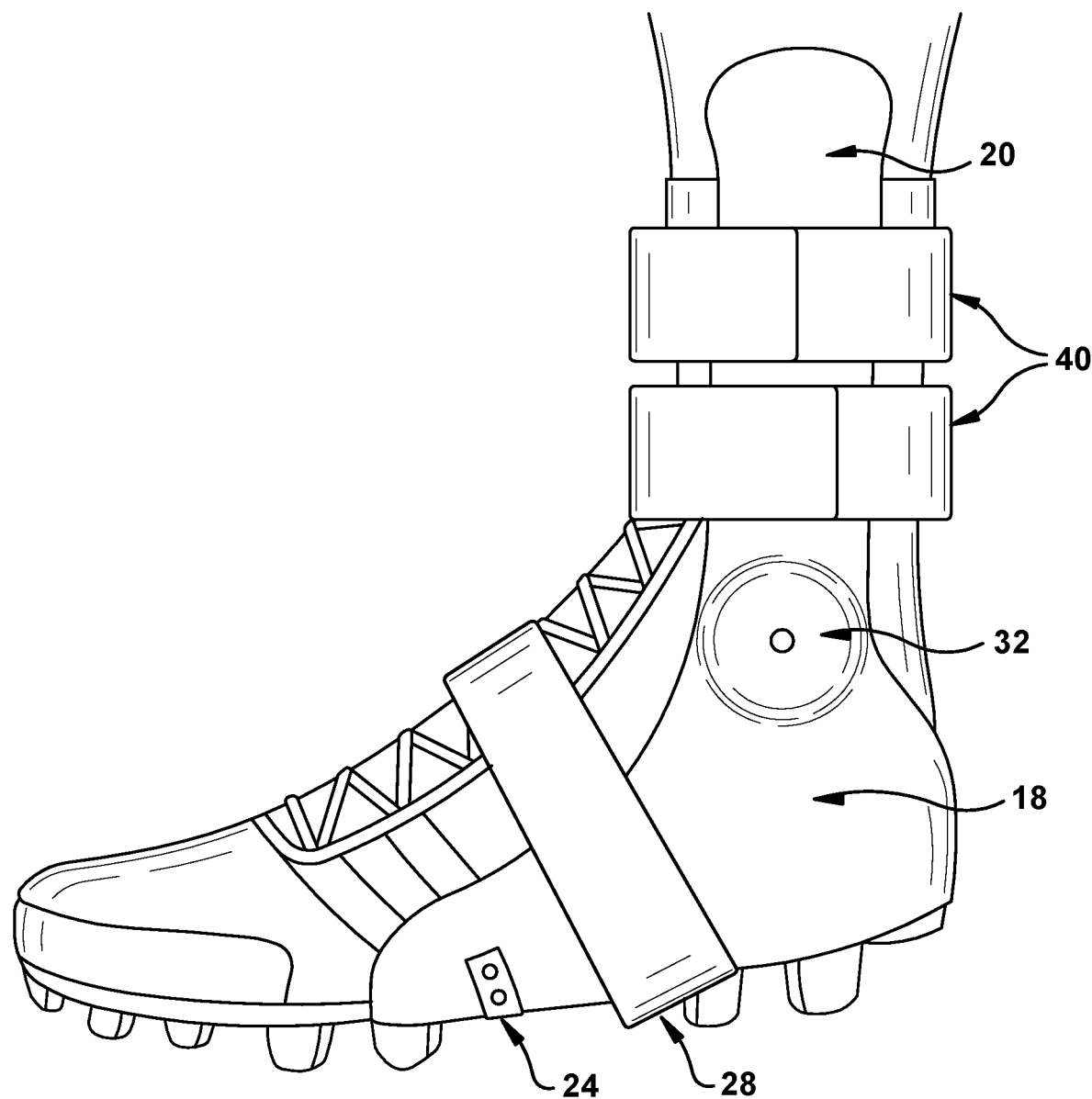
FIG. 1 is a lateral side view showing a first embodiment of the external ankle brace with an athletic shoe.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The invention comprises, consists of, or consists essentially of the following features, in any combination.

Ankle injuries are among the most common cause of lost playing time in a sporting career and although there are current preventative solutions, those current braces leave the user at risk for further injury because either the brace isn't strong enough to support the ankle or the shoe isn't fitted properly to the foot since "inside the shoe" braces tend to force the user to use a bigger shoe size. The present disclosure provides a rigid support and a much faster application time, all without compromising the fit of the shoe.

The present disclosure relates to an external ankle brace that is adapted to fit around a shoe to prevent and minimize injury to an ankle. The shoe having a heel portion, a sole, and oppositely disposed sides. The interaction between the external ankle brace and the shoe can be seen in FIG. 1.

Figure 2:
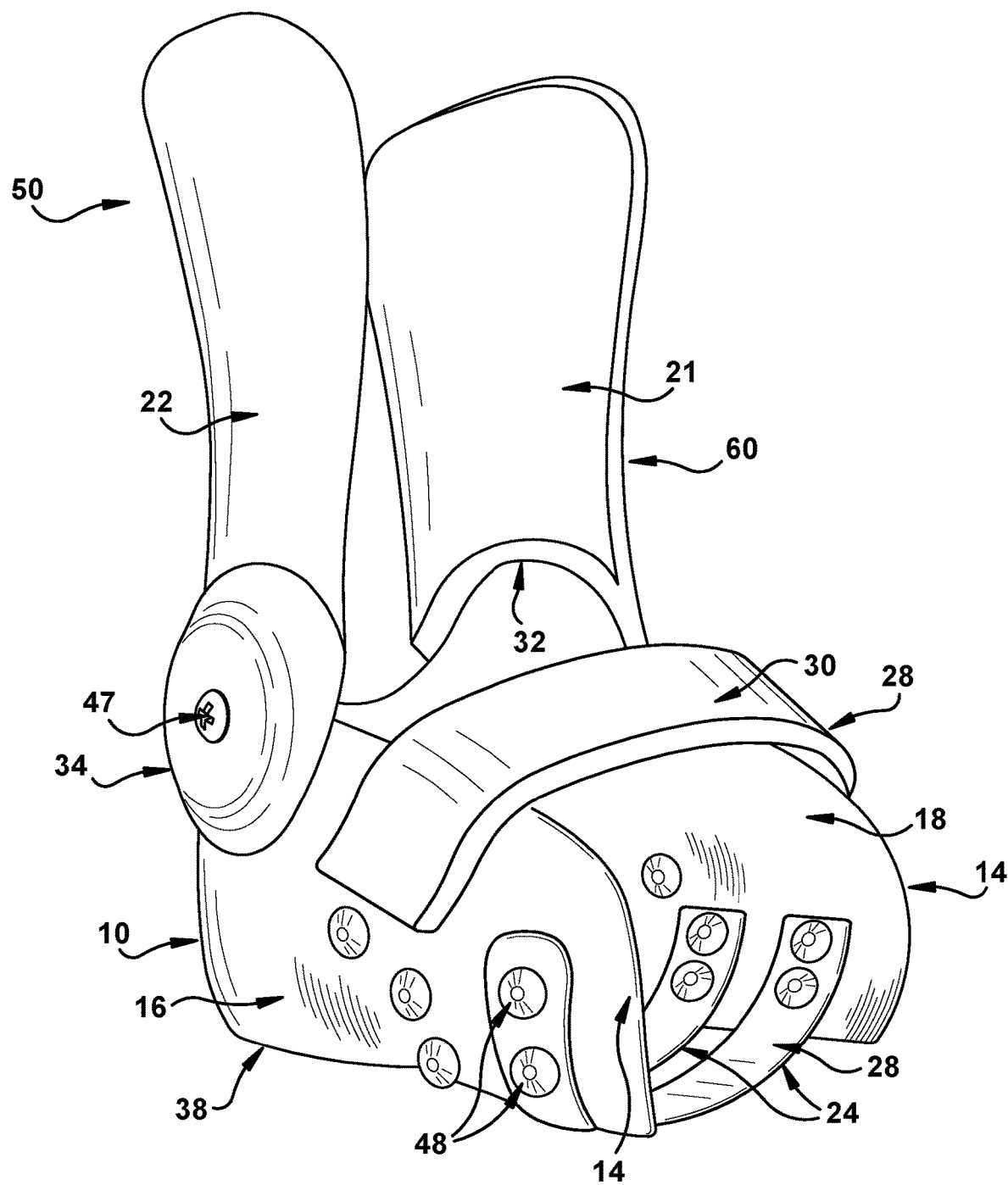
FIG. 2 is a perspective view of the external ankle brace of FIG. 1 from the medial side.

The external ankle brace of the present disclosure is generally indicated at 50 in FIG. 2. The external ankle brace 50 includes a rigid heel enclosure 10, a lateral upright extension 20, a medial upright extension 22, a lower fastening system 24, and an upper fastening system 28.

Figure 3:
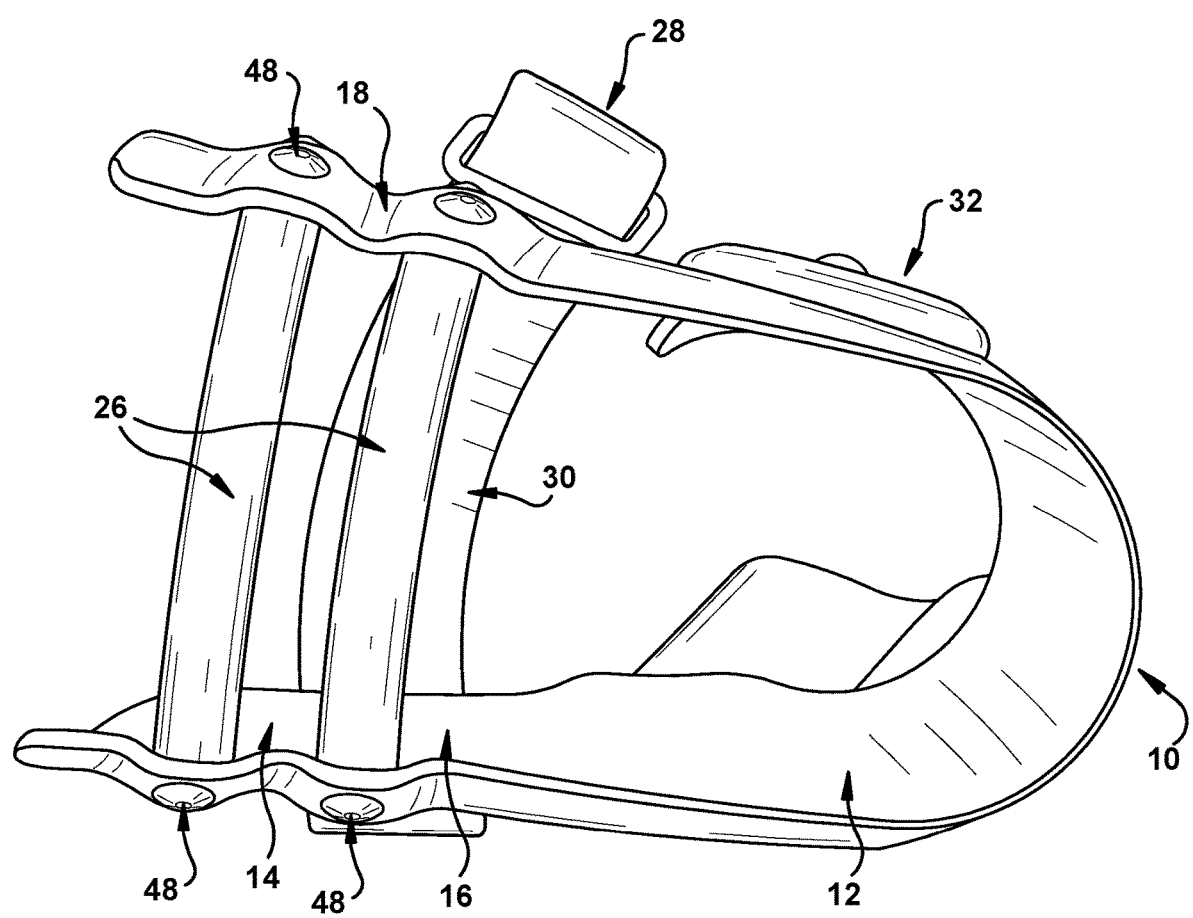
FIG. 3 is a perspective view showing the underside of the external ankle brace of FIG. 1.

The rigid heel enclosure 10 has a rear portion 12 (FIG. 3), for receiving the heel of the shoe, and a forward portion 14, for surrounding the sides of the shoe. The heel enclosure 10 may be made from rigid plastic pieces or any other suitable material. The forward portion 14 further includes a medial sidewall 16 and a lateral sidewall 18. The rigid heel enclosure 10 also has an upper end 36 (FIG. 2) for receiving the upright extensions 20 and 22, and a lower end 38 for surrounding the bottom of the shoe.

Figure 4:
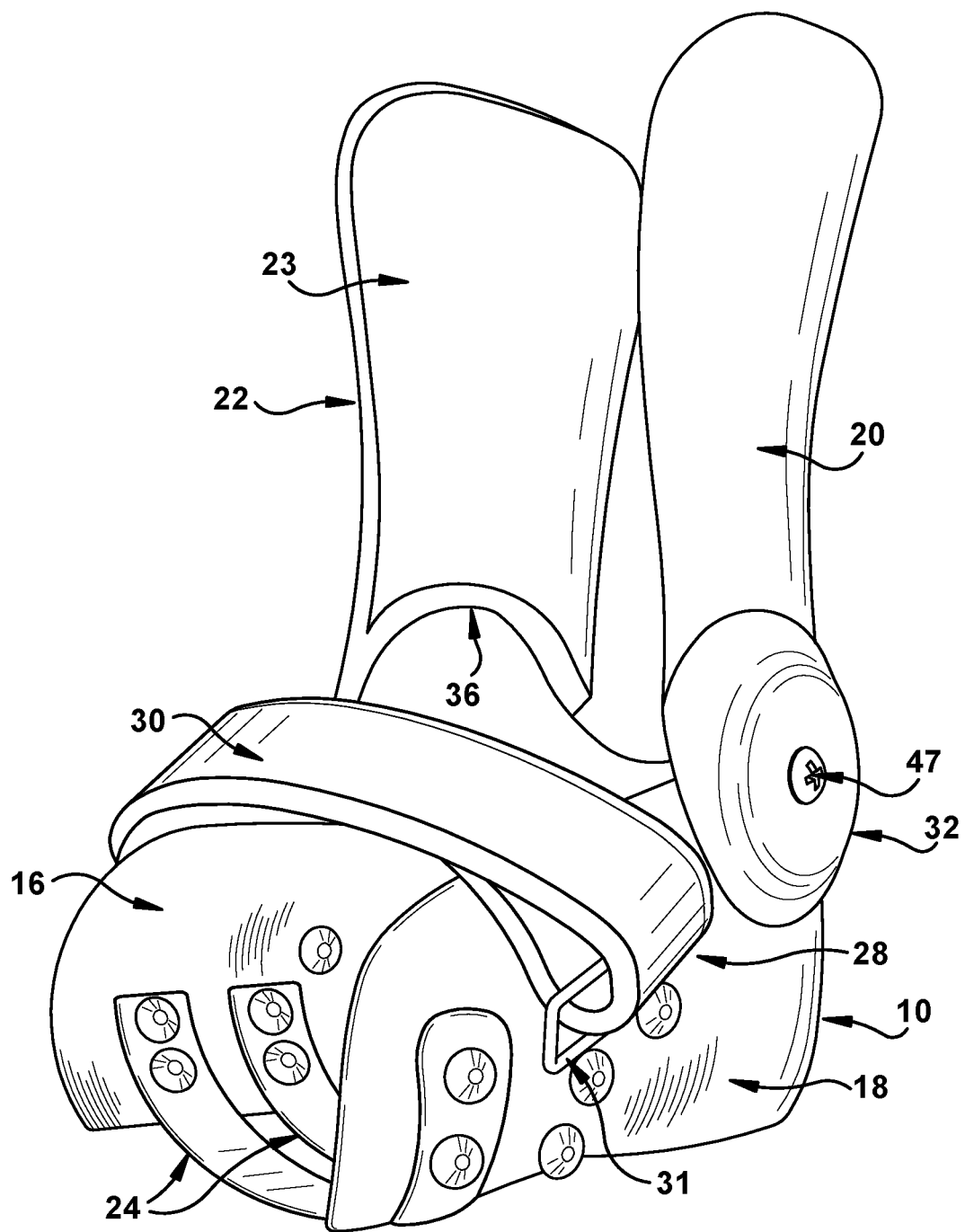
FIG. 4 is a perspective view of the external ankle brace of FIG. 1 from the lateral side.
Figure 5:
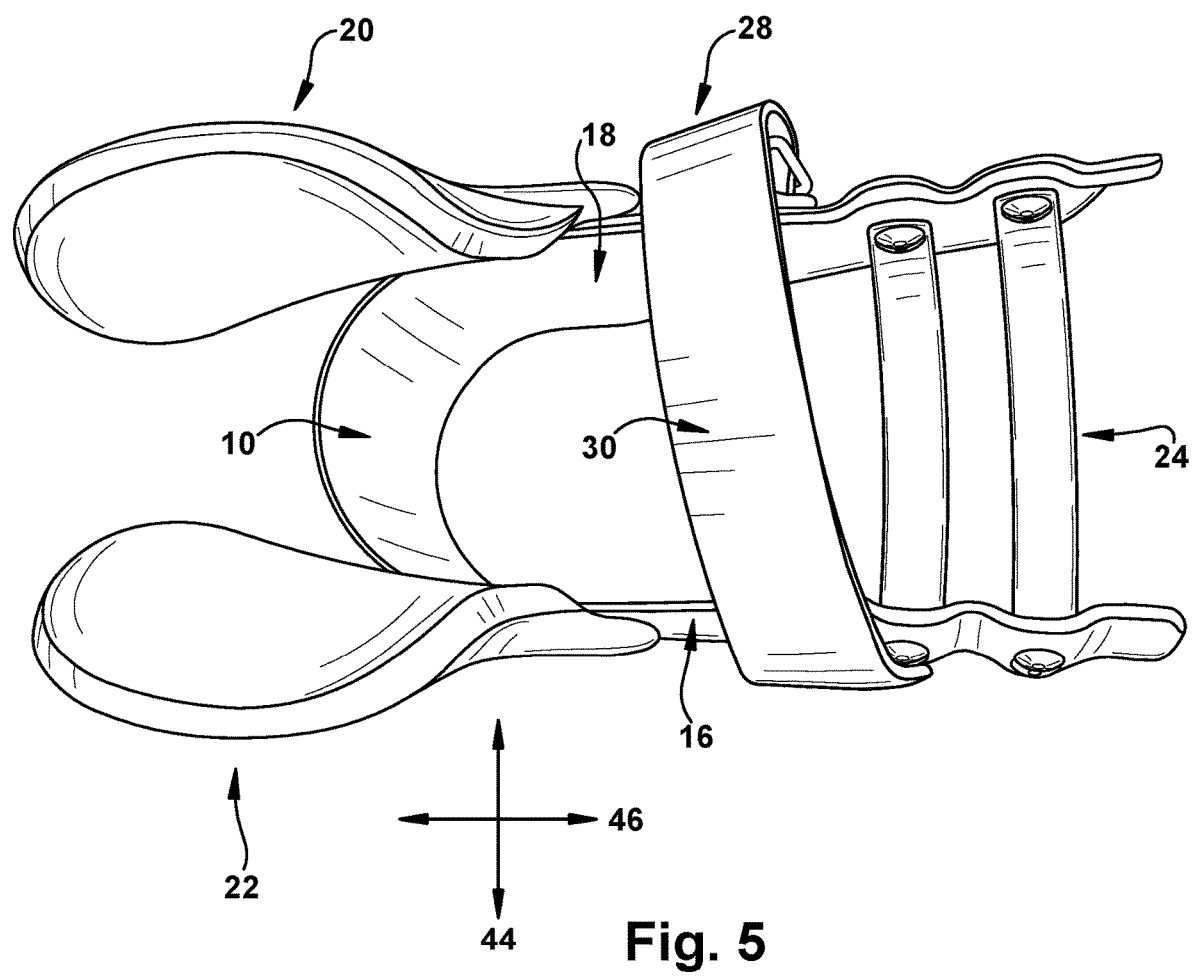
FIG. 5 is a top view of the external ankle brace of FIG. 1.
Figure 6:
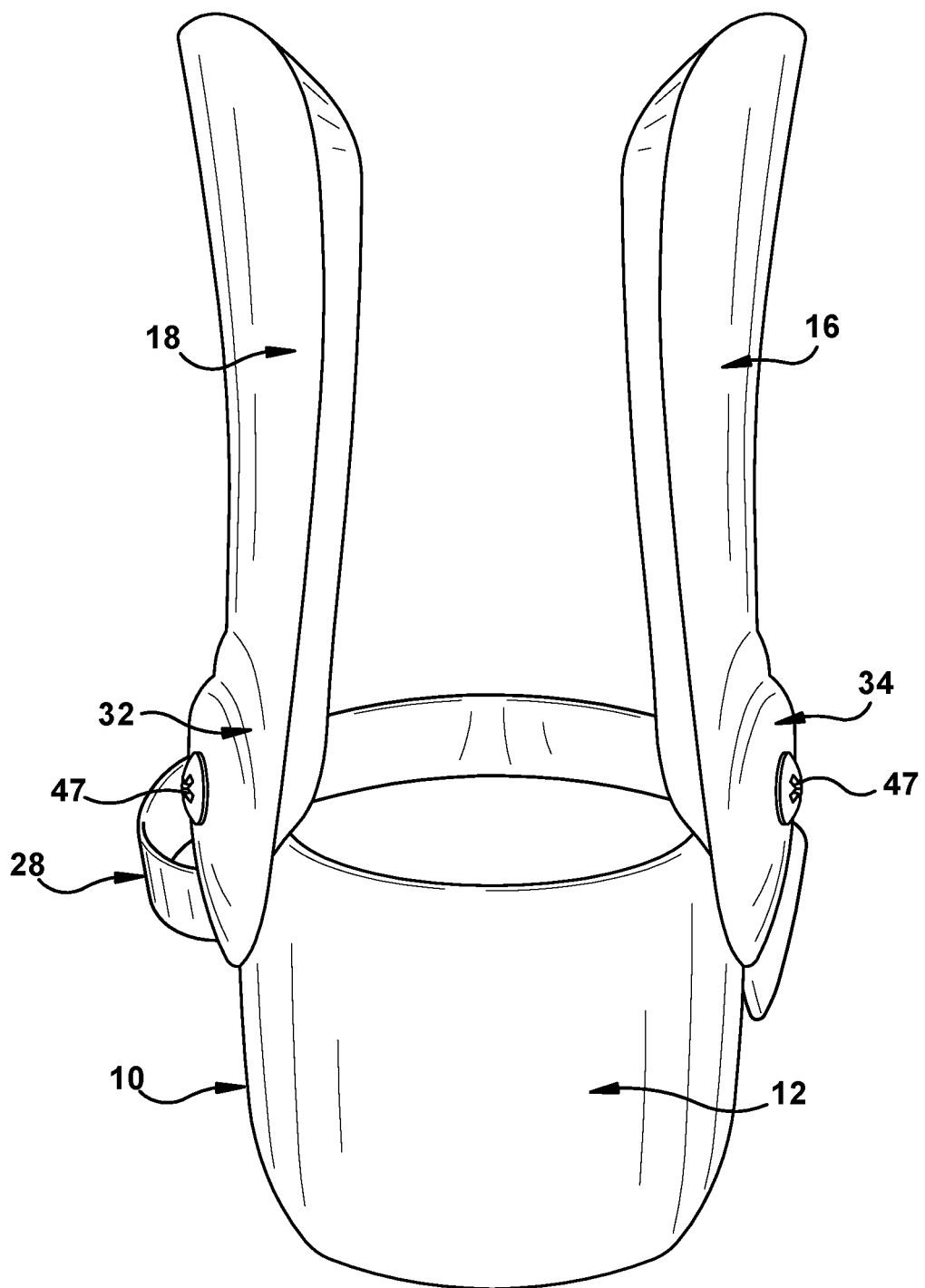
FIG. 6 is a rear view of the external ankle brace of FIG. 1.

The lateral upright extension 20 is oriented generally perpendicular to the rigid heel enclosure 10 and is pivotally attached to the lateral sidewall 18 at the upper end 36 by a lateral ankle joint 32 (FIG. 4). The joint allows the lateral upright extension 20 to rotate during motion giving the external ankle brace a less restrictive feel compared to previous braces. The lateral upright extension 20 may be made from plastic or any other suitable material. The lateral ankle joint 32 includes a fastener 47 and allows the lateral upright extension 20 to rotate relative to the lateral sidewall 18. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the lateral upright extension 20 has a concave shape for increased comfort for the user. The lateral upright extension 20 can also include foam padding on the interior side 21 (FIG. 2) of the lateral upright extension 20 to increase comfort and to allow a better fit for the user.

The medial upright extension 22 is perpendicular to the rigid heel enclosure 10 and is pivotally attached to the medial sidewall 16 at the upper end 36 by a medial ankle joint 34. The medial upright extension 22 may be made of rigid plastic or any other suitable material. The medial ankle joint 34 has a fastener 47 and allows the medial upright extension 22 to rotate relative to the medial sidewall 16. To adjust for anatomical positioning of the ankle, the medial ankle joint 34 is positioned closer to the upper end 36 than the position of the lateral ankle joint 32. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the medial upright extension 22 has a concave shape for increased comfort for the user. The medial upright extension 22 can also include foam padding on the interior side 23 (FIG. 4) of the medial upright extension to increase comfort and to allow a better fit for the user.

The lower fastening system 24 has at least one connecting strap 26 and at least one strap fastener 48 for connecting the lateral sidewall 18 to the medial sidewall 16 (FIG. 2) while passing underneath the sole of the shoe. Although the current embodiment uses a rubber strap 26, one having ordinary skill in the art would appreciate that plastic, nylon, or any other suitable strap type that is commonly known in the art could be used. Similarly, although the current embodiment uses rivets 48 to fasten the straps to each of the lateral and medial sidewalls 18 and 16 respectively, any other fastener could be used.

The upper fastening system 28 has at least one connecting strap 30 and at least one strap fastener 48 (FIG. 4) for removably connecting the lateral sidewall 18 to the medial sidewall 16 while passing over the top of the shoe. The upper fastening system further includes a D-ring 31 which is fixed on the lateral sidewall. The Velcro strap 30 is fixed to the medial sidewall and is looped through the D-ring 31 and overlaps back onto the strap 30. This allows for an adjustable fastening system to accommodate various sizes without compromising support. Although the current embodiment uses a Velcro strap 30 to removeably connect the sidewalls 16 and 18, one having ordinary skill in the art would appreciate that any kind of removable and adjustable strap can be used. Similarly, although the current embodiment only uses one connecting strap 30, any number of straps can be used to removably connect the sidewalls 16 and 18 over the top of the shoe.

As shown in FIG. 5, the external ankle brace 50 restricts movement of the ankle in the first directions indicated by arrows 44 and permits ankle movement in the second directions indicated by arrows 46.

Another embodiment (not shown) could include an upright fastening system 40 (FIG. 1), which would have at least one connecting strap for removably connecting the lateral upright extension 20 to the medial upright extension 22 above the ankle. This connecting strap could be Velcro or any other type of strap that would allow for an adjustable and removable connection.

Figure 7:
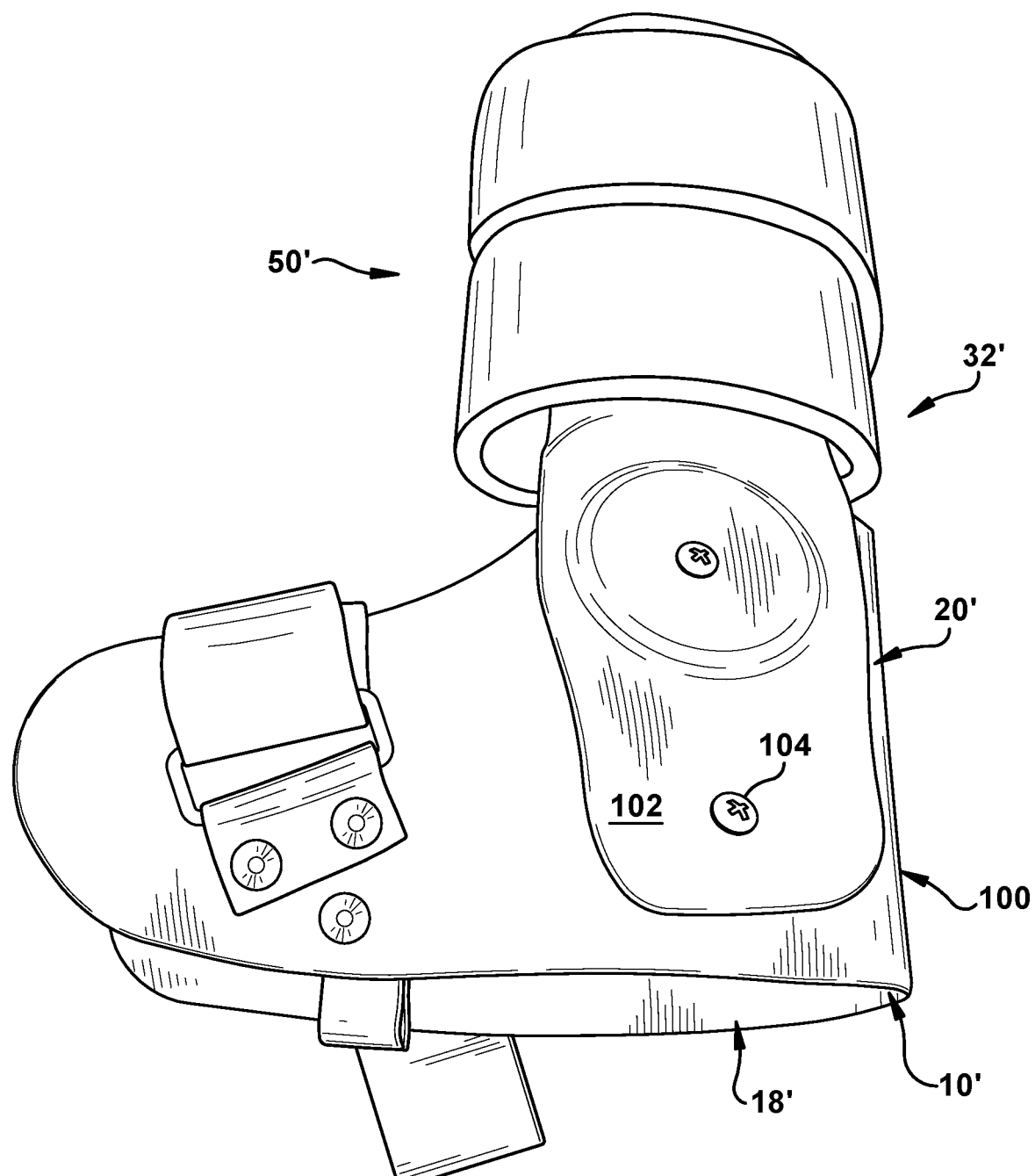
FIG. 7 is a lateral side view depicting a second embodiment of the external ankle brace.
Figure 8:
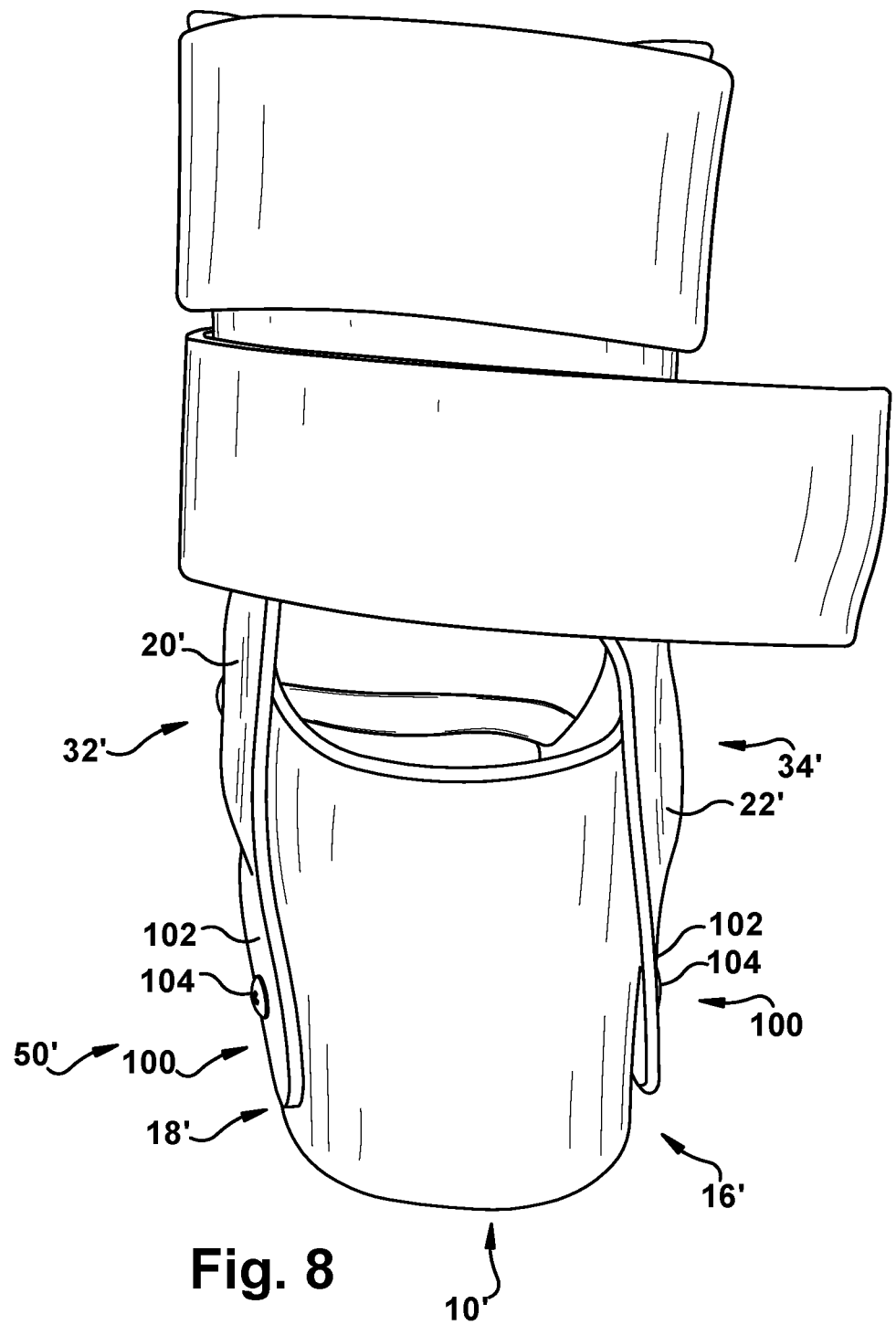
FIG. 8 is a rear view of the embodiment of FIG. 7.
Figure 9:
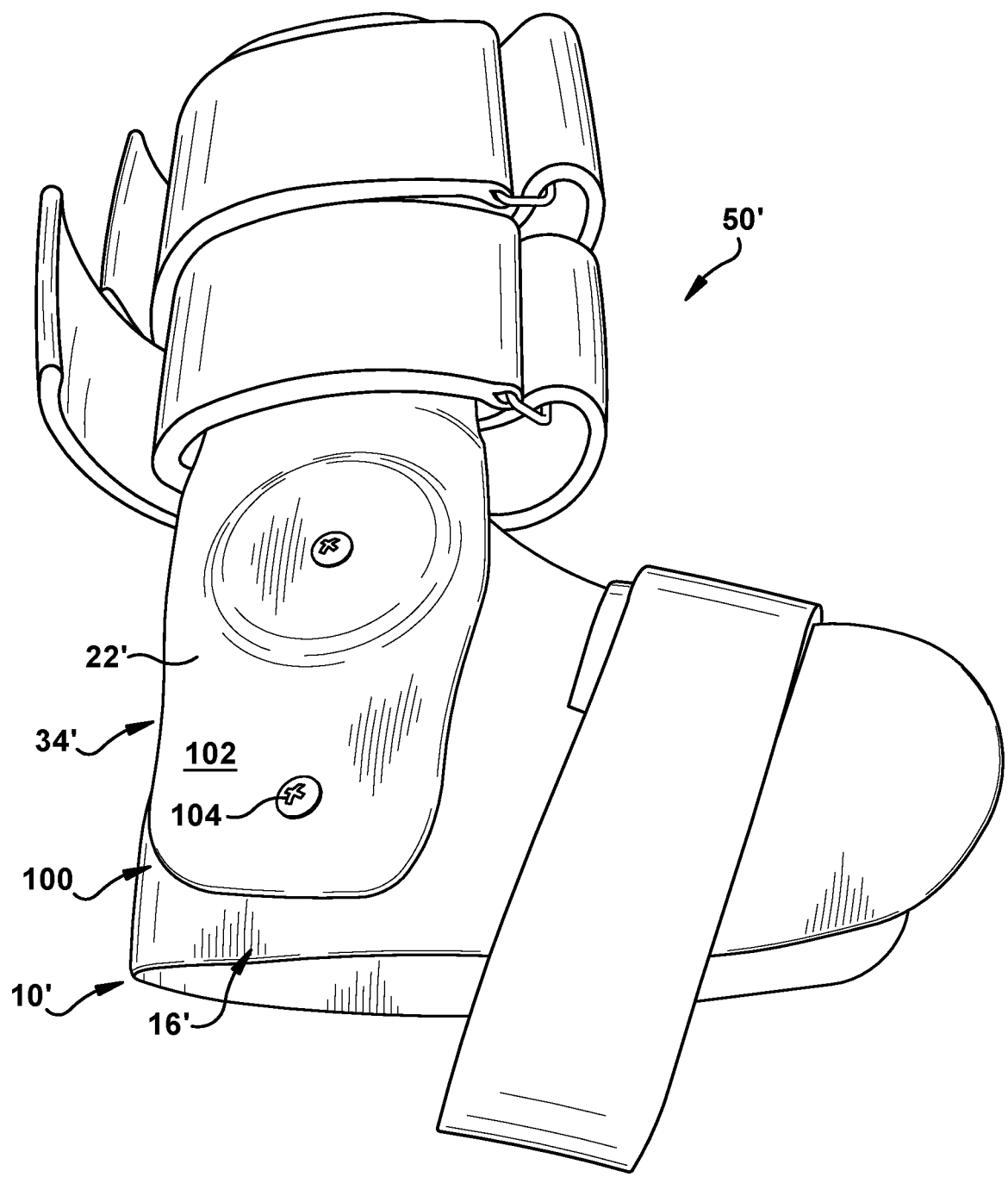
FIG. 9 is a medial side view of the embodiment of FIG. 7.

FIGS. 7-9 depict an external ankle brace 50' of a second embodiment. The external ankle brace 50' of FIGS. 7-9 is similar to the external ankle brace 50 of FIGS. 1-6 and therefore, structures of FIGS. 7-9 that are the same as or similar to those described with reference to FIGS. 1-6 have the same reference numbers with the addition of a "prime" mark. Description of common elements and operation similar to those in the previously described first embodiment will not be repeated with respect to the second embodiment.

In FIGS. 7-9, the external ankle brace 50' of the second embodiment, in contrast to that of the first embodiment, is configured with lateral and/or medial ankle joints 32' and 34' that selectively pivotally connect their corresponding lateral and/or medial upright extensions 20' and 22' to the corresponding lateral and/or medial sidewalls 18' and 16' and thus selectively allow the lateral and medial upright extensions 20' and 22' to move in the second direction relative to the heel enclosure 10'. Stated differently, the external ankle brace 50' of the second embodiment allows a user, or an associated medical professional, to "lock" pivoting of the external ankle brace 50' as desired, either for an entirety of the use/wear, or for a predetermined period of time during use of the external ankle brace 50' by the user. For example, the external ankle brace 50' could be prevented from the above-described pivotal movement in the second direction during an initial phase of healing of an injury, and then the external ankle brace 50' could be released to allow pivotal movement in the second direction once it is determined that such may be beneficial, or at least not detrimental, to the healing of that injury.

In order to provide such selective pivotal movement, the external ankle brace 50' of the second embodiment could include at least a chosen one (and/or both) of the lateral and medial upright extensions 20' and 22' which is selectively pivotally attached to a corresponding lateral or medial sidewall 18' and 16'. The chosen lateral and/or medial upright extensions 20' and 22' may include a pivot prevention feature 100 which is configured to selectively prevent pivoting of the chosen one of the lateral and medial upright extensions 20' and 22' with respect to the corresponding lateral or medial sidewall 18' and 16'.

As shown in FIGS. 7-9, the pivot prevention feature 100 may include a "tongue" or extension 102 from the corresponding lateral and/or medial upright extensions 20' and 22' downward toward the heel enclosure 10'. That extension 102 is then selectively secured to the corresponding lateral or medial sidewall 18' and 16' through use of a fastener 104, such as, but not limited to, the depicted screws. The combination of the extension 102, the fastener 104, and the lateral and medial sidewalls 18' and 16' then serves to inhibit or prevent pivoting or rotation of the lateral and/or medial upright extensions 20' and 22' with respect to the lateral or medial sidewalls 18' and 16'. While the extension 102 is shown as reaching substantially downward from a corresponding lateral and/or medial upright extensions 20' and 22' in FIGS. 7-9, it is also contemplated that the extension 102 could be oriented differently with respect to the remaining portions of the corresponding lateral and/or medial upright extensions 20' and 22', or the fastener 104 could be associated with the corresponding lateral and/or medial upright extensions 20' and 22' without the use of an extension 102, such as by extending the lateral and medial sidewalls 18' and 16' upward to allow placement of the fastener 104 above the lateral and/or medial ankle joints 32' and 34'.

The pivot prevention feature 100 depicted in the FIGS. is just one nonlimiting example, in fact, of any of a number of suitable mechanisms which can help with selectively inhibiting pivoting or rotation of the lateral and/or medial upright extensions 20' and 22' with respect to the lateral or medial sidewalls 18' and 16'. Other suitable mechanisms could include latches, frictional fit features, hooks, clips, straps, or any other structure which may be helpful in allowing selective prevention of at least some degree of rotation of the lateral and/or medial upright extensions 20' and 22' with respect to the lateral or medial sidewalls 18' and 16'. One of ordinary skill in the art will be able to provide a suitable pivot prevention mechanism 100 for a particular use environment of the external ankle brace 50'.

Embodiments can minimize ankle inversion and eversion during physical activity and/or minimize ankle medial and later rotation during physical activity and/or minimize ankle plantar flexion and dorsiflexion during physical activity and/or provide stability to the mid foot in limiting pronation and supination of the foot.

Embodiments can include a foot/ankle orthotic that includes a lateral sidewall, a medial sidewall, a heel enclosed backing connecting the sidewalls, a lateral upright extension, a medial upright extension and a bottom strapping system connecting sidewalls. The lateral and medial upright extensions are attached to the sidewalls with an overlapping ankle joint off-set to accommodate for medial and lateral malleolus anatomical positioning. The lateral sidewall coincides with the outer or exterior portion of the foot/ankle and the medial sidewall coincides with the inner portion of the foot/ankle. The lateral upright extension coincides with the outer or exterior portion of the lower leg and the medial upright extension coincides with the inner portion of the lower leg. Lateral and medial extension walls are configured to rise above the ankle of the wearer of the orthotic by approximately 8-9 inches (from the bottom of the hinge to the top of the extension walls). When donned by the wearer, lateral and medial side walls also partially wrap over the top or dorsum of the foot leaving a gap of approximately 3 to 4 inches between the sidewalls. The width of the medial and lateral upright extensions is approximately 3-4 inches wide.

A feature of an embodiment is to have the securing mechanism include a hook and loop strap across the dorsal (top) of the foot. This Velcro securing strap is riveted to the in place on both the medial and later side walls. A D ring is utilized on the lateral fixation in which the Velcro strap can be fed through and secured back upon itself. The lateral and medial upright extensions are secured by two removable Velcro straps and D rings. Male component Velcro is adhesively attached to each upright and the female component Velcro strap can connect to the uprights are desired positions for appropriate fitting. As an option, the brace may also be applied with various types of athletic adhesive tape in conjunction with or instead of the Velcro strapping and D ring system.

Another feature of an embodiment is an overlapping ankle joint hinge to allow the ankle to move freely through plantar flexion and dorsiflexion. The overlapping ankle joint is located on the medial and lateral aspects of the gauntlet where the medial and lateral side bodies attach with the medial and lateral uprights respectively. The ankle joint hinge components are off set to produce a more anatomically correct gauntlet for a more fluid mobility.

Foam padding (approximately X inch) is attached to the inside of both the medial and lateral uprights to provide additional comfort and protection for the wearer. The gauntlet is sized so that one size can fit multiple size shoes. A separate gauntlet is needed to accommodate both right and left ankles.

A sheet of vacuum formable thermoplastic large enough to cover the entire mold is cut and placed in an oven to be heated to a formable temperature. These are several types and thicknesses of plastic that may be used for this fabrication including orthotic grade polypropylene, polyethylene, and copolymer.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

What is claimed is:

1. An external ankle brace, comprising:
a heel enclosure having a rear portion and a forward portion, wherein
the external ankle brace is disposed on the exterior of a shoe, the shoe having a heel portion, a sole, and oppositely disposed sides, said rear portion is configured for receiving the heel of the shoe, and said forward portion includes a medial sidewall and a lateral sidewall for surrounding the sides of the shoe, each of the medial and lateral sidewalls having a proximal portion extending continuously from the rear portion of the heel enclosure, the medial and lateral sidewalls each being configured to extend from the heel portion of the shoe in a longitudinal direction beyond a talus of a wearer's foot and toward the toe, each of the medial and lateral sidewalls having a distal portion longitudinally spaced from the proximal portion of the corresponding medial or lateral sidewall such that the distal portion is at least partially located adjacent to an instep area of a corresponding medial or lateral side of the shoe and the distal portions of the medial and lateral sidewalls are spaced apart, and
the external ankle brace further comprises:
a lateral upright extension selectively perpendicular to at least the lateral sidewall of said heel enclosure and pivotally attached to the proximal portion of the lateral sidewall;
a medial upright extension selectively perpendicular to at least the medial sidewall of said heel enclosure and pivotally attached to the proximal portion of the medial sidewall;
a lower fastening system comprising at least one connecting strap for connecting the distal portion of the lateral sidewall to the distal portion of the medial sidewall underneath the sole of the shoe longitudinally forward of the talus of the wearer's foot; and
an upper fastening system comprising at least one connecting strap extending from said lateral sidewall to said medial sidewall across the top of the shoe,
wherein at least a chosen one of the lateral or medial upright extensions is selectively pivotally attached to a corresponding lateral or medial sidewall, the at least a chosen one of the lateral or medial upright extensions including a pivot prevention feature configured to selectively prevent pivoting of the at least a chosen one of the lateral or medial upright extensions with respect to the corresponding lateral or medial sidewall, and
wherein the at least one connecting strap of the upper fastening system is configured to connect to the lateral sidewall and medial sidewall longitudinally forward of the talus of the wearer's foot.

2. The external ankle brace as set forth in claim 1, further including a lateral ankle joint that selectively pivotally connects said lateral upright extension to said lateral sidewall and selectively allows said lateral upright extension to move relative to said heel enclosure.

3. The external ankle brace as set forth in claim 2, wherein said lateral ankle joint in combination with said lateral upright extension and said heel enclosure prevent movement of the ankle in a direction different from the direction of movement relative to said heel enclosure.

4. The external ankle brace as set forth in claim 2, further including a medial ankle joint that selectively pivotally connects said medial upright extension to said medial sidewall and selectively allows said medial upright extension to move relative to said heel enclosure.

5. The external ankle brace as set forth in claim 4, wherein said medial ankle joint in combination with said medial upright extension and said heel enclosure prevent movement in another direction.

6. The external ankle brace as set forth in claim 4, wherein said heel enclosure further includes oppositely disposed upper and lower ends, where said medial ankle joint is positioned closer to said upper end than the position of said lateral ankle joint.

7. The external ankle brace as set forth in claim 1, wherein:
the medial sidewall is completely inside the medial upright extension.

8. The external ankle brace as set forth in claim 1, wherein the brace is configured to minimize plantar flexion and dorsiflexion during physical activity.

9. The external ankle brace as set forth in claim 1, wherein:
the heel enclosure receives the upright extensions.

10. The external ankle brace as set forth in claim 1, further comprising:
a first connecting structure extending from the lateral sidewall to the lateral upright extension; and
a second connecting structure extending from the medial sidewall to the medial upright extension.

11. The external ankle brace as set forth in claim 1, wherein:
the shoe is located in the heel enclosure; and
the shoe is an athletic shoe.

12. The external ankle brace as set forth in claim 1, wherein:
the shoe is located in the brace, and the shoe is a laced shoe, and the shoe is located directly between the medial and lateral sidewalls, and the heel enclosure is plastic and encloses a heelcap of the shoe.

13. The external ankle brace as set forth in claim 1, wherein:
the external ankle brace is configured so that respective portions of the medial and lateral sidewalls extend in a manner that the wearer's foot, when the external ankle brace is worn by the wearer and the shoe is disposed in the external ankle brace and the foot is in the shoe, is not located directly between the medial and lateral sidewalls.

14. The external ankle brace as set forth in claim 1, wherein:
the external ankle brace is configured so that respective portions of the medial and lateral sidewalls extend in a manner that the wearer's foot, when the external ankle brace is worn by the wearer, is located directly between the medial and lateral sidewalls and the medial and lateral sidewalls extend from the heel portion of the shoe in the longitudinal direction to respective locations beyond the talus of the wearer's foot and toward the toe with the foot directly located in between the respective locations.

15. The external ankle brace as set forth in claim 1, wherein:
the external ankle brace is configured so that the rear portion extends about a rear of the shoe above the heel portion of the shoe when the ankle brace is worn by the wearer.

16. The external ankle brace as set forth in claim 1, wherein:
a bottom surface of the heel enclosure continuously extends from a tip of the distal portion of the lateral sidewall, to a proximal portion of the lateral sidewall, to the rear portion, to a proximal portion of the medial sidewall and then to a tip of the distal portion of the medial sidewall.

17. The external ankle brace as set forth in claim 1, wherein:
the shoe is located in the external ankle brace and located directly between the medial and lateral sidewalls; and
the medial sidewall and the lateral sidewall are curved with respect to the vertical direction to curve about respective sides of the shoe.

18. The external ankle brace as set forth in claim 1, wherein the lateral upright extension and the medial upright extension are directly connected to respective portions of the lateral sidewall and the medial sidewall which extend substantially longitudinally from the rear portion.

19. The external ankle brace as set forth in claim 1, wherein:
the external ankle brace is configured so that respective portions of the medial and lateral sidewalls extend in a manner that the wearer's foot, when the external ankle brace is worn by the wearer, is located directly between the medial and lateral sidewalls.

20. The external ankle brace as set forth in claim 1, wherein:
the at least one connecting strap of the lower fastening system includes a portion that is located between the medial sidewall and the lateral sidewall.

21. The external ankle brace as set forth in claim 1 wherein the at least one strap of the upper fastening system extends from the lateral sidewall to the medial sidewall in an arc that is at least substantially vertical.

22. The external ankle brace as set forth in claim 1, further comprising:
an upright fastening system comprising at least one connecting strap for removably connecting said lateral upright extension to said medial upright extension above the ankle, wherein the at least one connecting strap for removably connecting said lateral upright extension to said medial upright extension above the ankle is totally located outside of the upright extensions.

23. An external ankle brace, comprising:
a lower leg section configured to interface with a leg of a human at a lower leg thereof; and
a foot section configured to interface with a shoe worn on a foot of the human at locations where the foot of the human is located, wherein
the external ankle brace is configured to be disposed on the exterior of the shoe of the human, the shoe having a heel portion, a sole, an upper portion with oppositely disposed sides, and a toe section, the heel portion being at a rear of the shoe, and the toe section being at a front of the shoe,
the foot section is established by a body that is configured to receive the rear of the shoe and straddle both a lateral and a medial side of the foot while establishing respective openings at the bottom of the foot and the top of the foot,
the lower leg section includes a lateral upright extension that includes a portion that extends upward away from the foot section, the lateral upright extension being rotationally attached to the foot section,
the lower leg section includes a medial upright extension that includes a portion that extends upward away from the foot section, the medial upright extension being rotationally attached to the foot section, and
the external ankle brace further includes:
a lower fastening system comprising at least one connecting strap connecting one side of the body on one side of the foot to an opposite side of the body on an opposite side of the foot and extending underneath the sole of the shoe;
an upper fastening system comprising at least one connecting strap connecting the one side of the body to the opposite side of the body across the top of the shoe; and
a lower leg section fastening system comprising at least one connecting strap connecting said portion of said medial upright extension that extends upwardly away from the foot section with said portion of said lateral upright extension that extends upwardly away from the foot section,
wherein the at least one connecting strap of the upper fastening system is configured to connect to a lateral sidewall and a medial sidewall of the body longitudinally forward of a talus of the human's foot.

24. The external ankle brace as set forth in claim 23, wherein:
the foot section is established by a portion that includes a first subportion, a second subportion and a third subportion, the first subportion of the foot section being configured to receive the rear of the shoe, the second subportion of the foot section extending away from the first subportion towards the toe section on the medial side of the foot when the brace is worn by the human, the third subportion of the foot section extending away from the first subportion towards the toe section on the lateral side of the foot when the brace is disposed on the exterior of the shoe and the foot is in the shoe.

25. The external ankle brace as set forth in claim 24, wherein:
the shoe is an athletic shoe; and
the shoe is located in the external ankle brace and located directly between the second subportion and the third subportion; and
the second subportion and the third subportion are contoured to respective sides of the athletic shoe.

26. The external ankle brace as set forth in claim 25, wherein:
the second subportion and the third sub portion also extend below the foot when the brace is disposed on the exterior of the shoe and the foot is in the shoe.

27. The external ankle brace as set forth in claim 24, wherein the lateral upright extension extends downward past an upper portion of the third subportion of the foot section and the medial upright extension extends downward past an upper portion of the second subportion of the foot section, and wherein the upper portion of the third subportion extends forward and backward from the lateral upright extension at a lowest level of the lateral upright extension, and wherein the upper portion of the second subportion extends forward and backward from the medial upright extension at a lowest level of the medial upright extension.

28. The external ankle brace as set forth in claim 23, further including a medial ankle joint that pivotally connects said medial upright extension to said foot section and allows said medial upright extension to move relative to said foot section and a lateral ankle joint that pivotally connects said lateral upright extension to said foot section and allows said lateral upright extension to move relative to said foot section, and wherein said medial ankle joint is positioned higher than the position of said lateral ankle joint.

29. The external ankle brace as set forth in claim 23, wherein the foot section is made of plastic and is a monolithic body.

30. The external ankle brace as set forth in claim 23, wherein:
the lateral upright extension and the medial upright extension are respectively made of plastic and have respective concave shapes.

31. The external ankle brace as set forth in claim 23, wherein the brace is a means for minimizing ankle medial and lateral rotation during physical activity.

32. The external ankle brace as set forth in claim 23 wherein the at least one connecting strap of the lower leg section fastening system extends completely around a lower leg of the human when the brace is worn by the human.

33. The external ankle brace as set forth in claim 23, wherein the brace is a means for providing stability to the mid foot by limiting pronation and supination of the foot.

34. The external ankle brace as set forth in claim 23 wherein the foot section is made of orthotic grade polymer and is a monolithic body.

35. The external ankle brace as set forth in claim 23, wherein the brace is a means for minimizing ankle inversion and eversion during physical activity.

36. The ankle brace of claim 23, the foot section consisting of a U shaped structure.

37. The ankle brace of claim 23, wherein the strap of the lower fastening system is riveted to one of the sidewalls.

38. The external ankle brace as set forth in claim 23, wherein:
the at least one connecting strap of the lower fastening system is attached to the one side of the body by a rivet and attached to the opposite side of the body by a rivet.

39. The external ankle brace as set forth in claim 23, wherein:
the at least one connecting strap of the lower fastening system is permanently attached to the one side of the body and permanently attached to the opposite side of the body.

40. Footwear, comprising:
the external ankle brace of claim 23; and
the shoe, wherein
the shoe is a shoe with cleats.

41. An ankle brace configured to be used with a shoe, the ankle brace comprising:
a body extending, with respect to the shoe when the shoe is in the ankle brace, from a first side of the shoe, around a back of the shoe, to a second side of the shoe opposite the first side of the shoe, the body having a medial sidewall and a lateral sidewall extending about the sides of the shoe, the medial sidewall and the lateral sidewall extending at least to a location of an instep area of a corresponding medial and lateral side, respectively, of the shoe;
a lateral upright extension pivotally attached to the lateral sidewall;
a medial upright extension pivotally attached to the medial sidewall; and
a fastening system including at least one connecting strap for removably connecting said lateral sidewall to said medial sidewall, the at least one connecting strap of the fastening system being attached to the sidewalls at a location completely forward respective forward most portions of the upright extensions when the upright extensions are perpendicular with respective directions of extension of the sidewalls, wherein
the ankle brace is an external ankle brace configured for use completely exterior to the shoe, and provide for support without compromising fit of the shoe, and wherein at least a chosen one of the lateral or medial upright extensions is pivotally attached to a corresponding lateral or medial sidewall, and wherein the at least one connecting strap is configured to connect to the lateral sidewall and the medial sidewall above a wearer's foot and longitudinally forward of a talus of the wearer's foot.

42. The external ankle brace as set forth in claim 41, wherein the at least a chosen one of the lateral or medial upright extensions includes a pivot prevention feature configured to selectively prevent pivoting of the at least the chosen one of the lateral or medial upright extensions with respect to the corresponding lateral or medial sidewall and thus maintain the at least a chosen one of the lateral or medial upright extensions in a fixed orientation.

43. The external ankle brace as set forth in claim 42, wherein:

the fastening system is an upper fastening system; and the ankle brace includes a lower fastening system including at least one connecting strap for connecting the lateral sidewall to the medial sidewall underneath the shoe beneath the instep area of the shoe.

44. The external ankle brace as set forth in claim 43, wherein:

the at least one connecting strap of the upper fastening system connects said lateral sidewall to said medial sidewall across the top of the shoe.

45. The external ankle brace as set forth in claim 44, wherein:

the ankle brace provides for rigid support without compromising fit of the shoe.

46. The external ankle brace as set forth in claim 41, wherein:

the fastening system includes an upper fastening subsystem;

the upper fastening sub-system includes the least one connecting strap, the at least one connecting strap extending across the top of the shoe.

47. The external ankle brace as set forth in claim 41, wherein:

the fastening system includes a lower fastening subsystem;

the lower fastening sub-system includes the least one connecting strap, the at least one connecting strap extending underneath the sole of the shoe.

48. The external ankle brace as set forth in claim 41, wherein:

the connecting strap extends from over across the top of the shoe to below the body.

49. The external ankle brace as set forth in claim 41, wherein:

the shoe is in the ankle brace and the shoe has a sole; and the connecting strap extends from over across the top of the shoe to below the body and below the sole of the shoe.

50. The external ankle brace as set forth in claim 49, wherein:

the shoe includes cleats extending from the sole of the shoe.

51. The external ankle brace as set forth in claim 41, wherein:

the sidewalls have a silhouette of a shoe when viewed from respective sides of the brace.

52. The external ankle brace as set forth in claim 41, wherein the brace is a means for minimizing plantar flexion and dorsiflexion during physical activity.

53. The external ankle brace as set forth in claim 41, wherein:

the lateral sidewall smoothly transitions from a distal portion of the lateral sidewall to a location on a proximal portion of the lateral sidewall above an uppermost portion of the lateral sidewall midway between a front and a rear of the brace when viewed from the side, the front being closer to a toe section of the shoe than a rear when the shoe is located in the brace.

54. The ankle brace of claim 41, wherein the body is rigid.

55. The ankle brace of claim 41, wherein the body is plastic.

56. An apparatus, comprising:

means for receiving a heel of a shoe and for surrounding sides of a shoe;

means for connecting a first side of the means for receiving and surrounding to a second side of the means for receiving and surrounding;

means for interfacing with a wearer of the shoe above the shoe, wherein the apparatus is an ankle brace, the means for interfacing with the wearer of the shoe above the shoe includes a first sub-component connected at a first location to the means for receiving the heel of the shoe and for surrounding sides of the shoe, the means for interfacing with the wearer of the shoe above the shoe includes a second sub-component connected at a second location to the means for receiving the heel of the shoe and for surrounding sides of the shoe, the first location is at a medial side of the means for receiving the heel of the shoe and the second location is at a lateral side of the means for receiving the heel of the shoe, and the apparatus is configured to enable a wearer of the ankle brace to selectively (i) permit at least one of the first sub-component or the second sub-component to pivot relative to the means for receiving a heel of a shoe and for surrounding sides of a shoe and (ii) lock the at least one of the first sub-component or the second sub-component so that the at least one of the first sub-component or the second sub-component is prevented from pivoting relative to the means for receiving a heel of a shoe and for surrounding sides of a shoe, wherein the means for connecting is configured to connect the first side of the means for receiving and surrounding to the second side of the means for receiving and surrounding over a top of the shoe and longitudinally forward of a talus of a foot of the wearer.

* * * * *